United States Patent
McFarland

(10) Patent No.: US 10,625,050 B2
(45) Date of Patent: Apr. 21, 2020

(54) REDUCED-INSERTION FORCE MICROINTRODUCER

(71) Applicant: C. R. Bard, Inc., Murray Hill, NJ (US)

(72) Inventor: Todd P. McFarland, Herriman, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 277 days.

(21) Appl. No.: 15/458,829

(22) Filed: Mar. 14, 2017

(65) Prior Publication Data

US 2017/0265891 A1 Sep. 21, 2017

Related U.S. Application Data

(60) Provisional application No. 62/308,809, filed on Mar. 15, 2016.

(51) Int. Cl.
*A61M 25/00* (2006.01)
*A61M 29/00* (2006.01)
*A61B 17/88* (2006.01)
*A61M 25/06* (2006.01)
*A61B 17/34* (2006.01)

(52) U.S. Cl.
CPC ..... *A61M 25/0068* (2013.01); *A61B 17/8811* (2013.01); *A61M 25/0009* (2013.01); *A61M 25/0067* (2013.01); *A61M 25/0662* (2013.01); *A61M 29/00* (2013.01); *A61B 17/3417* (2013.01); *A61B 17/3421* (2013.01); *A61M 2025/0687* (2013.01)

(58) Field of Classification Search
CPC .............. A61M 25/0068; A61M 29/00; A61M 25/0067; A61M 2025/0687; A61B 17/3421; A61B 17/3417
See application file for complete search history.

(56) References Cited

U.S. PATENT DOCUMENTS

| | | | | |
|---|---|---|---|---|
| 2003/0216770 A1* | 11/2003 | Persidsky | .......... | A61B 17/3423 606/191 |
| 2006/0052749 A1* | 3/2006 | Moyer | ............... | A61B 17/3421 604/160 |
| 2011/0144580 A1* | 6/2011 | Pang | .................. | A61B 17/3415 604/96.01 |

(Continued)

FOREIGN PATENT DOCUMENTS

WO WO-2015122218 A1 * 8/2015

*Primary Examiner* — Amber R Stiles
(74) *Attorney, Agent, or Firm* — Rutan & Tucker LLP

(57) ABSTRACT

An introducer used to provide a route through which a catheter or other medical device is inserted so as to gain access to a subcutaneous vessel of a patient is disclosed. The introducer is configured so as to minimize the amount of force needed to enter and dilate a vessel, thus reducing trauma to the vessel and the patient. In one embodiment, an introducer is disclosed, comprising a sheath and a dilator. The sheath includes a tubular portion that defines a lumen. The dilator includes an elongate body and a tapered distal tip and is configured to be removably disposed within the lumen of the tubular portion of the sheath. The dilator elongate body defines a cylindrical recess proximally extending from the tapered distal tip. The cylindrical recess configured to receive therein the tubular portion of the sheath when the dilator is disposed within the tubular portion of the sheath.

17 Claims, 6 Drawing Sheets

(56) References Cited

U.S. PATENT DOCUMENTS

2013/0184736 A1* 7/2013 Aman ............... A61M 25/0074
606/191
2016/0346072 A1* 12/2016 Kawashima .......... A61F 2/0095

* cited by examiner

REDUCED-INSERTION FORCE MICROINTRODUCER

CROSS-REFERENCE TO RELATED APPLICATIONS

This application claims the benefit of U.S. Provisional Patent Application No. 62/308,809, filed Mar. 15, 2016, and entitled "Reduced-Insertion Force Microintroducer," which is incorporated herein by reference in its entirety.

BRIEF SUMMARY

Briefly summarized, embodiments of the present invention are directed to a microintroducer that is used to provide a route through which a catheter or other medical device is inserted so as to gain access to a subcutaneous vessel of a patient. The introducer is configured so as to minimize the amount of force needed penetrate the skin and vessel and to dilate the vessel, thus reducing trauma to the vessel and the patient.

In one embodiment, an introducer is disclosed, comprising a sheath and a dilator. The sheath includes a tubular portion that defines a lumen. The dilator includes an elongate body and a tapered distal tip and is configured to be removably disposed within the lumen of the tubular portion of the sheath. The dilator elongate body defines a cylindrical recess proximally extending from the tapered distal tip. The cylindrical recess configured to receive therein the tubular portion of the sheath when the dilator is disposed within the tubular portion of the sheath.

In another embodiment, undulations are included on the perimeter of the distal end of the tubular portion of the sheath so as to distribute insertion forces as the introducer is inserted into the patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a microintroducer ("introducer") that is used to provide a route through which a catheter or other medical device can be inserted so as to gain access to a vessel of a patient, for instance. In accordance with present embodiments, the introducer is configured so as to minimize the amount of force needed to enter and dilate a vessel, thus reducing trauma to the vessel and the patient.

Figure 1A:
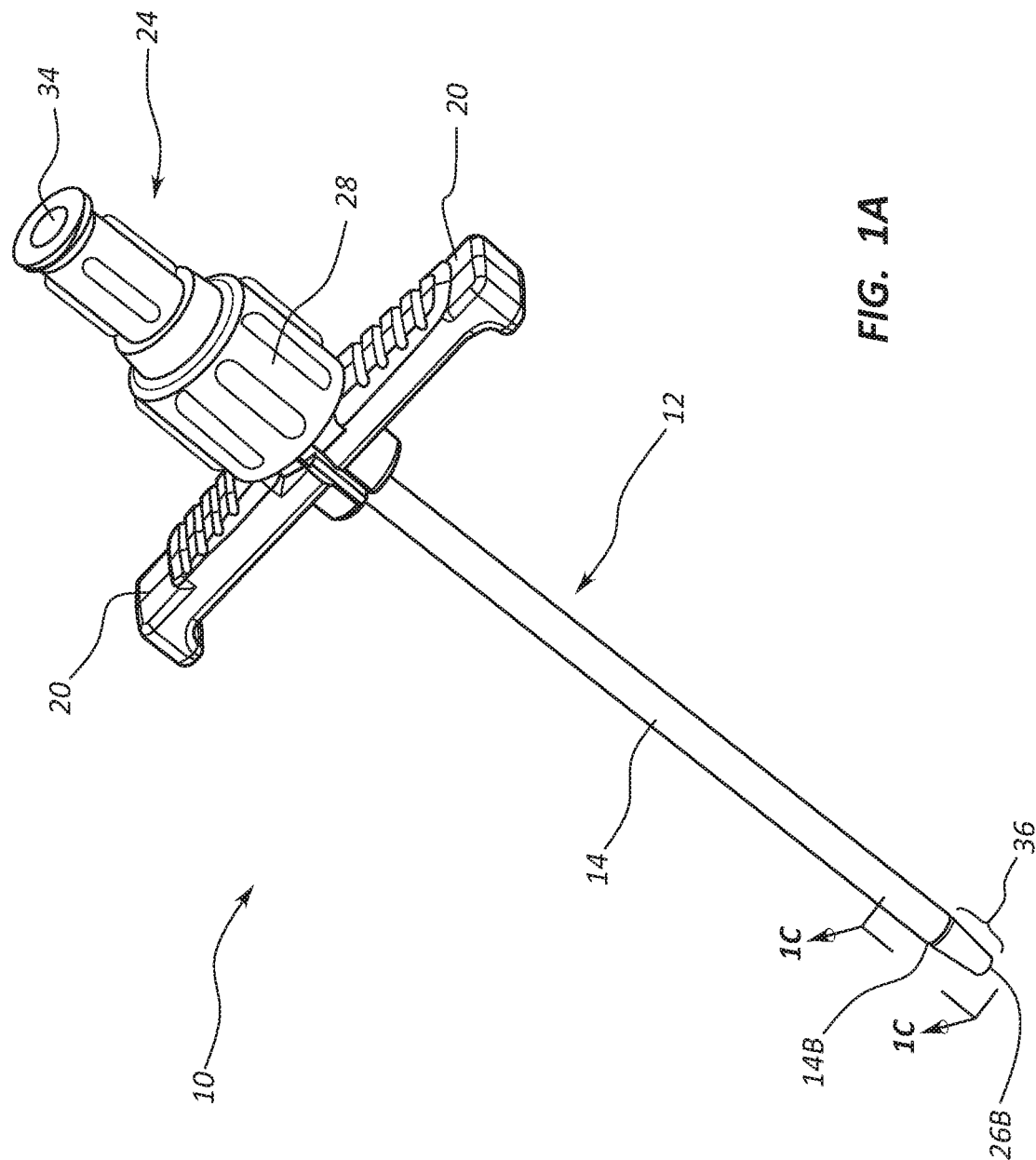
FIGS. 1A-1C are various view of an introducer according to one embodiment.
Figure 1B:
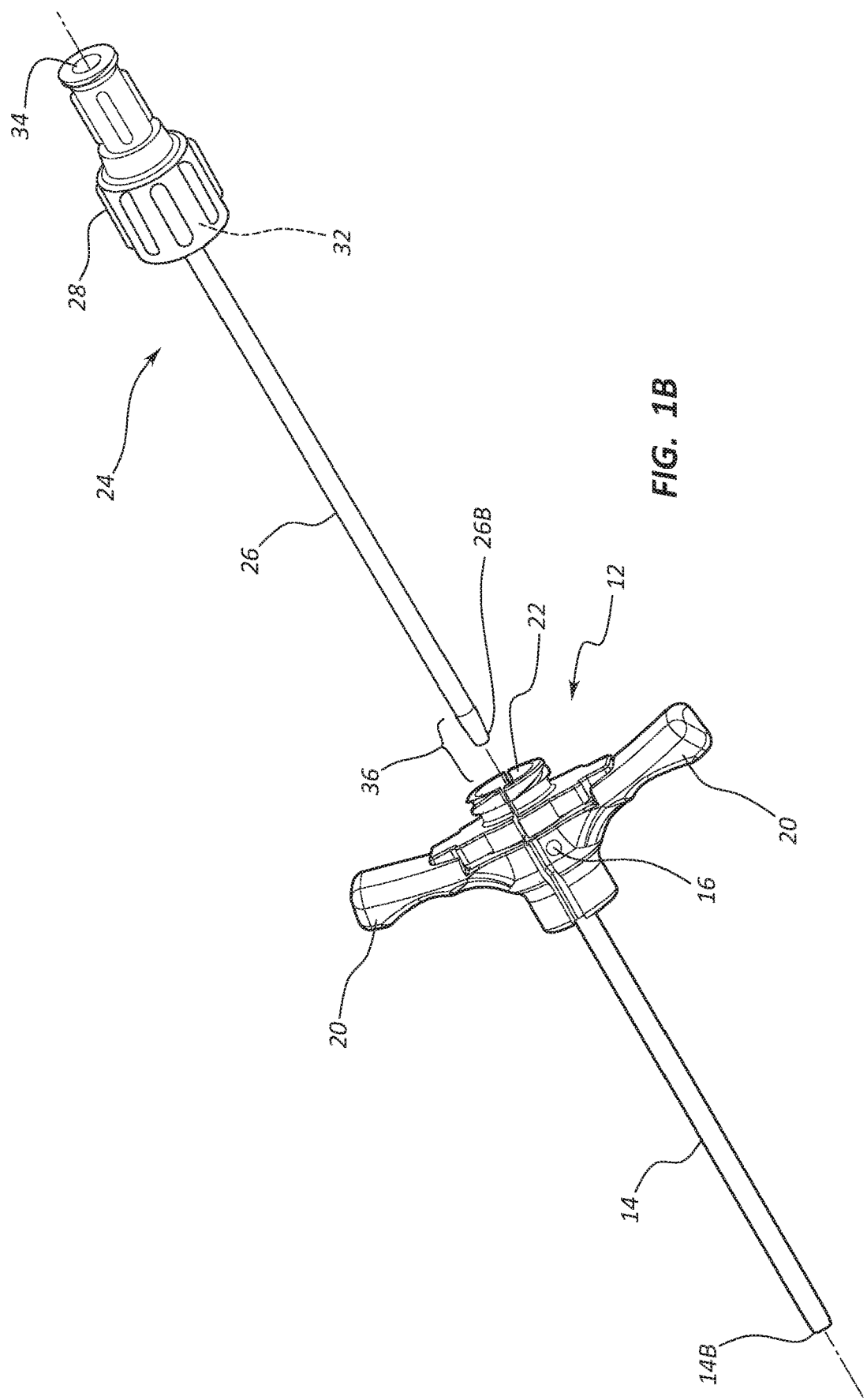
Figure 1C:
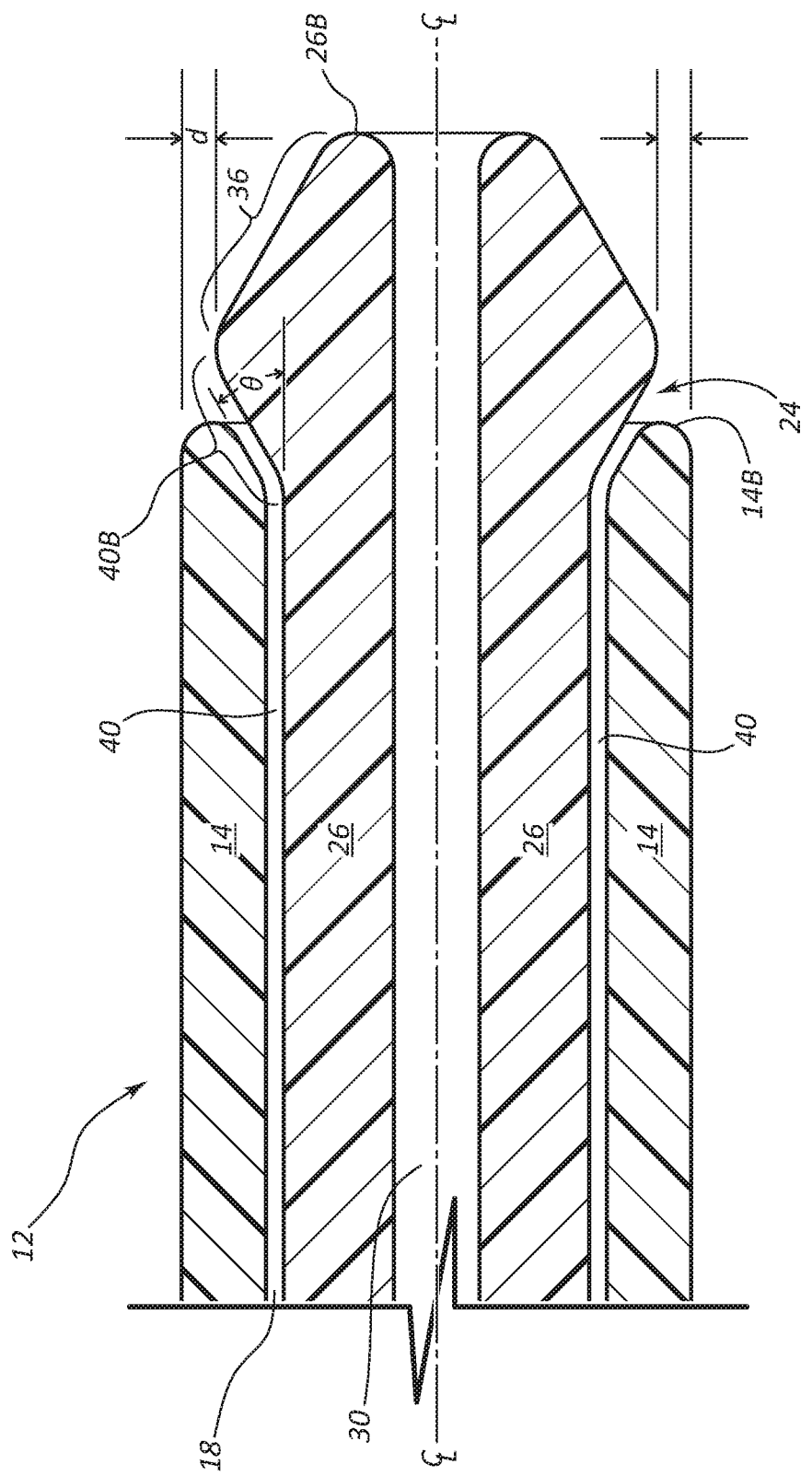

FIGS. 1A-1C depict an introducer (e.g., introducer, microintroducer), generally designated at 10, according to one embodiment. As shown, the introducer 10 generally includes a sheath 12 and a dilator 24. In greater detail, the sheath 12 includes an elongate tubular portion 14 that extends from a hub 16. The tubular portion 14 distally extends from the hub 16 to terminate at a distal end 14B thereof, and cooperates with the hub to define a lumen 18 that extends from the open distal end of the tubular portion to a threaded opening 22 on the hub. Handles 20 are also included on the hub 16.

The dilator 24 includes an elongate portion 26 that extends from a hub 28. The elongate portion 26 distally extends from the hub 28 to terminate at a distal end 26B thereof, and cooperates with the hub to define a central guidewire channel 30 that extends from the open distal end of the elongate portion to an opening 34 disposed at the proximal end of the hub. The guidewire channel 30 is centered about a centerline of the introducer 10 (FIG. 1C), in the present embodiment, which corresponds with a longitudinal axis of the dilator elongate portion. The hub 28 further includes a threaded cavity 32 that is configured to threadably connect with the threaded opening 22 of the sheath 12 when the sheath and dilator 24 are mated together, as shown in FIG. 1A.

As best seen in FIG. 1C, the dilator elongate portion 26 includes a tapered tip 36 proximally extending from the distal end 26B thereof. In accordance with the present embodiment, the dilator elongate portion 26 further defines a cylindrical recess 40 disposed proximal to the tapered tip 36 so as to extend therefrom proximally to the dilator hub 28. The recess 40 is centered about the centerline (FIG. 1C) of the introducer 10 in the present embodiment and is configured so as to reduce the outer diameter of the dilator elongate portion 26 proximal to the tapered tip 36. This in turn enables the sheath tubular portion 14 to seat within the recess 40, which reduces the outer diameter profile of the sheath tubular portion. This results in relatively smooth dilator-to sheath transition profile, easing its percutaneous insertion through a skin insertion site and into a subcutaneous vessel, resulting in less trauma and damage to the vessel.

In greater detail, the tubular portion 14 of the sheath 12 seats within the recess 40 as shown in FIG. 1C such that only a portion of the tubular portion extends radially beyond the outer diameter of the tapered tip 36; this portion is indicated by a difference distance d in FIG. 1C. Absent the recess 40, the tubular portion would radially extend a distance greater than d, which would cause the introducer 10 to have an undesirably greater cross-sectional profile during introducer insertion into the patient. Instead, the introducer configuration shown in FIGS. 1A-1C provides a smaller cross-sectional insertion profile and relatively less traumatic introducer insertion into the patient body. Further, the recess 40 enhances a smooth transition between the tapered tip 36 and the distal end 14B of the sheath tubular portion 14, thus ensuring a smooth introducer introduction into the patient body via an insertion site in the skin and a vessel of the patient. Note that the thickness of the outer wall of the sheath tubular portion 14 in the embodiment shown in FIG. 1C is greater than the distance d such that a portion of the tubular portion is received within the cylindrical recess 40, as shown.

In the present embodiment, the tubular portion 14 of the sheath 12 includes polytetrafluoroethylene ("PTFE"), though other suitable materials may also be employed. The elongate portion 26 of the dilator 24 includes high-density polyethylene ("HDPE"), though again other suitable materials may be employed. The sheath tubular portion wall thickness is about 0.001 inch in one embodiment, though other thicknesses are also possible in other embodiments.

FIG. 1C shows that a distal end 40B of the recess 40 of the elongate portion of the dilator 24, which is defined at a location proximal to the tapered tip 36, is slanted to define an acute angle theta, θ, with a horizontal line substantially parallel to the longitudinally extending centerline shown in FIG. 1C. The slanted nature of the of the recess distal end 40B assists in proximally withdrawing the tapered tip 36 of the dilator elongate portion 26 past the distal end 14B of the sheath tubular portion 14 during withdrawal of the dilator through the lumen 18 of the sheath tubular portion. Note that the surface of the sheath tubular portion distal end 14B that opposes the recess distal end 40B is correspondingly angled so as to match the angled configuration of the recess distal end to further assist the passage of the dilator tapered distal end 36 past the distal end 14B of the sheath tubular portion 14.

Figure 2:
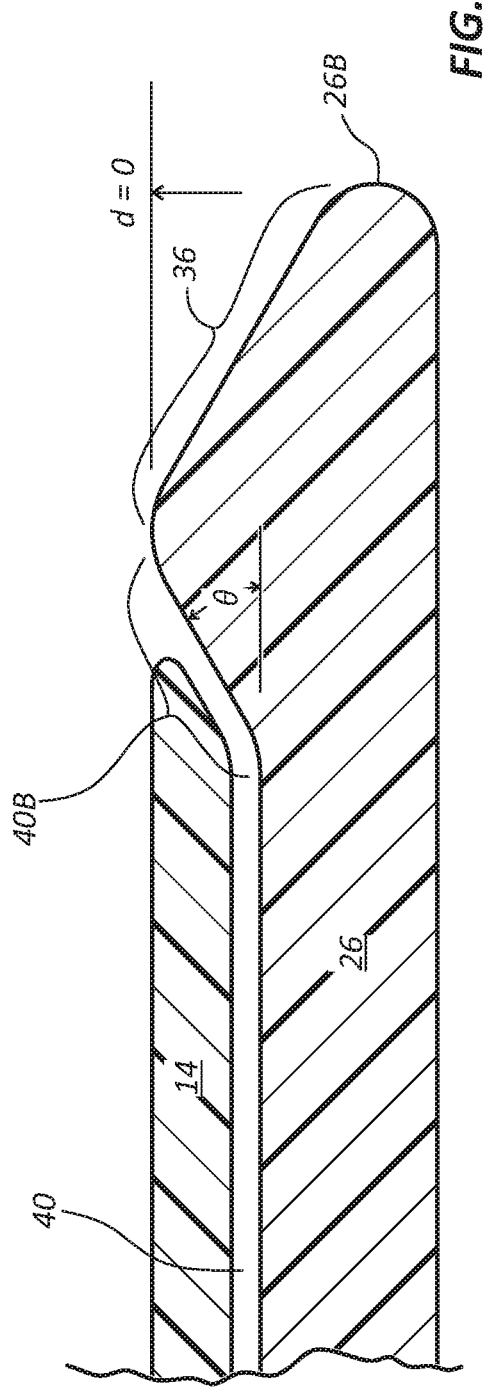
FIG. 2 is a partial cross-sectional side view of an introducer according to one embodiment.
Figure 3:
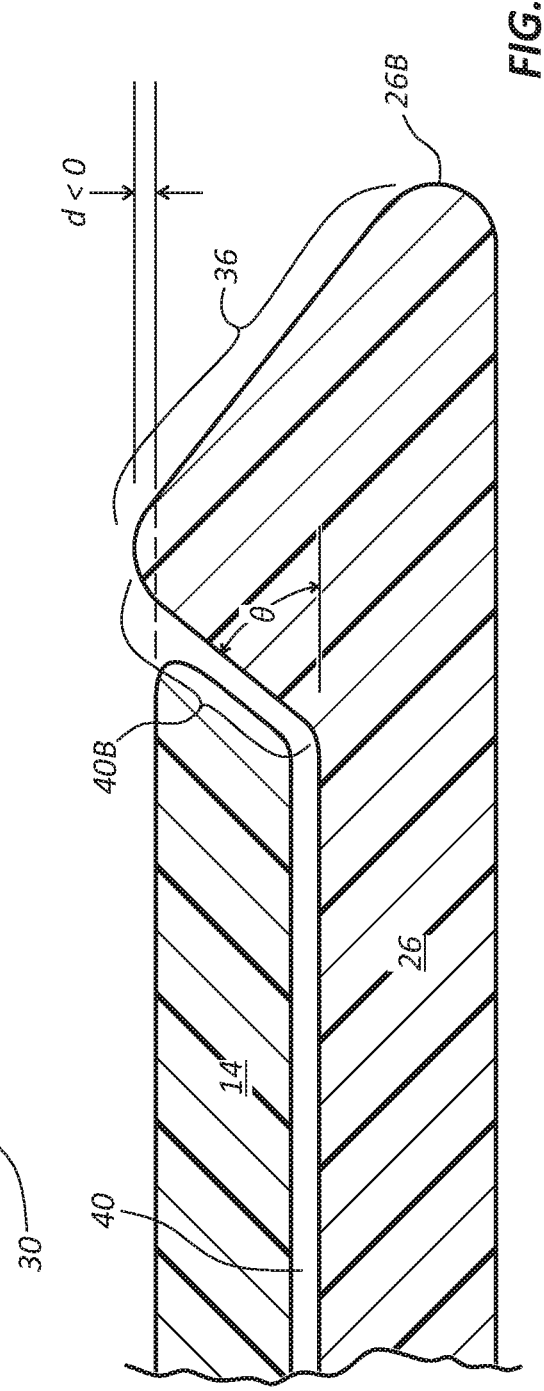
FIG. 3 is a partial cross-sectional side view of an introducer according to one embodiment.
Figure 4:
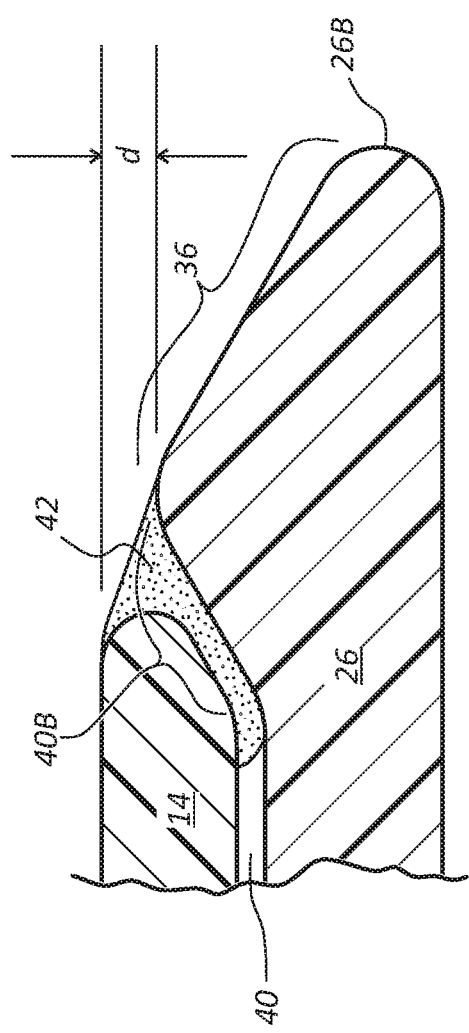
FIG. 4 is a partial cross-sectional side view of an introducer according to one embodiment.

A variety of angled configurations for the distal end 40B of the recess 40 of the elongate portion of the dilator 24 is possible in other embodiments, as shown in FIGS. 2 and 3, for example. In detail, FIG. 2 shows the distal end 40B of the dilator recess 40 defining an angle θ that is shallower relative to the angle shown in FIG. 1C. In contrast, FIG. 3 shows the distal end 40B of the dilator recess 40 defining an angle θ that is steeper relative to the angle shown in FIG. 1C. As before, the surface of the sheath tubular portion distal end 14B that opposes the recess distal end 40B is correspondingly angled so as to match the angled configuration of the recess distal end. Indeed, in the embodiments shown in FIGS. 1C-3, the angles defined by the recess distal end 40B and the sheath tubular portion distal end 14B are substantially equal, though they can differ in other embodiments. Thus, these and other modifications to the distal portion of the introducer 10 are contemplated.

It is appreciated that, in the present embodiment, the guidewire channel 16 is disposed coaxially central to both the sheath 12 and the dilator 14, though it can be disposed in other positional configurations in other embodiments. Also, the recess 40 is coaxially disposed with respect to the guidewire channel 30 of the dilator elongate portion 26 in the present embodiment.

FIG. 2 shows further details of the cylindrical recess 40 defined by the dilator elongate portion 26 according to one embodiment, wherein the recess is sized such that the outer diameter of the sheath tubular portion 14 radially extends a distance that is substantially equal to the outer diameter of the tapered tip 36 of the dilator elongate portion, thus making the difference distance d substantially equal to zero, as shown. As with the previous embodiment, this provides a relatively reduced cross-sectional profile for insertion of the introducer 10 into the patient body via an insertion site.

FIG. 3 shows further details of the cylindrical recess 40 defined by the dilator elongate portion 26 according to one embodiment, wherein the recess is sized such that the outer diameter of the sheath tubular portion 14 radially extends a distance that is less relative to the outer diameter of the tapered tip 36 of the dilator elongate portion, thus providing a net negative difference distance d, as shown. As with the previous embodiment, this provides a relatively reduced cross-sectional profile for insertion of the introducer 10 into the patient body via an insertion site. In light of the above, it is appreciated that the difference distance d can be varied according to design to be less than zero, greater than zero, or equal to zero, according to the manner shown in FIGS. 1A-3.

Note that the embodiments shown in FIGS. 1A-1C, 2, and 3 the depth of the cylindrical recess 40 can be modified at time of manufacture to vary the difference distance d. In other embodiments, the thickness of the wall of the tubular portion 14 can be varied as needed during manufacture to produce a desired value of d. In yet other embodiments, a combination of tubular portion wall thickness and recess depth can be modified to achieve a desired difference distance d.

As FIG. 2 shows, in one embodiment a filler 42 can be included in the gap or space between the tapered tip 36 and the distal end 14B of the sheath tubular portion 14 to provide a smooth transition between the tapered tip and the tubular portion. The filler 42 can include a biocompatible material, including a gel, a resin, or epoxy, for instance, and including a bind strength low enough to enable separation when the dilator 14 is to be removed from the sheath 12 during use. In one embodiment, the filler 42 is dissolvable when in contact with a liquid, such as blood or water, such that solid remnants of the filler are not carried into the bloodstream during use of the introducer 10.

Note that in the embodiment shown in FIGS. 1A-1C, the cylindrical recess 40 extends proximally from the tapered tip 36 to the hub 28 of the dilator 24, though in other embodiments the recess can extend to other points along the elongate portion 26 of the dilator. It is appreciated that the cylindrical recess 40 can be defined on the dilator elongate portion via any one of suitable manufacturing processes, including molding, machining, extrusion, cutting, casting, etc.

Figure 5:
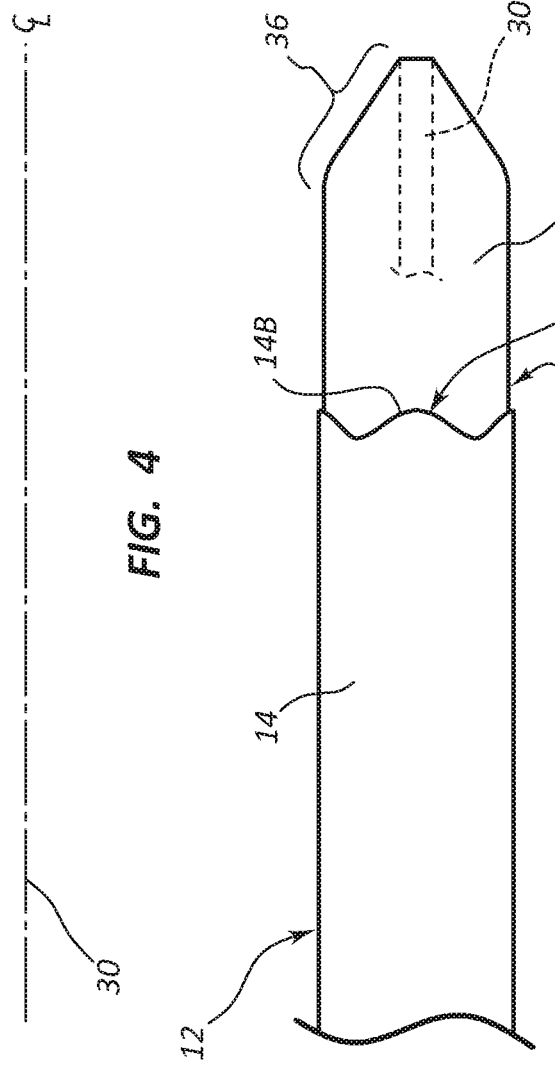
FIG. 5 is a side view of an introducer according to one embodiment.
Figure 6:
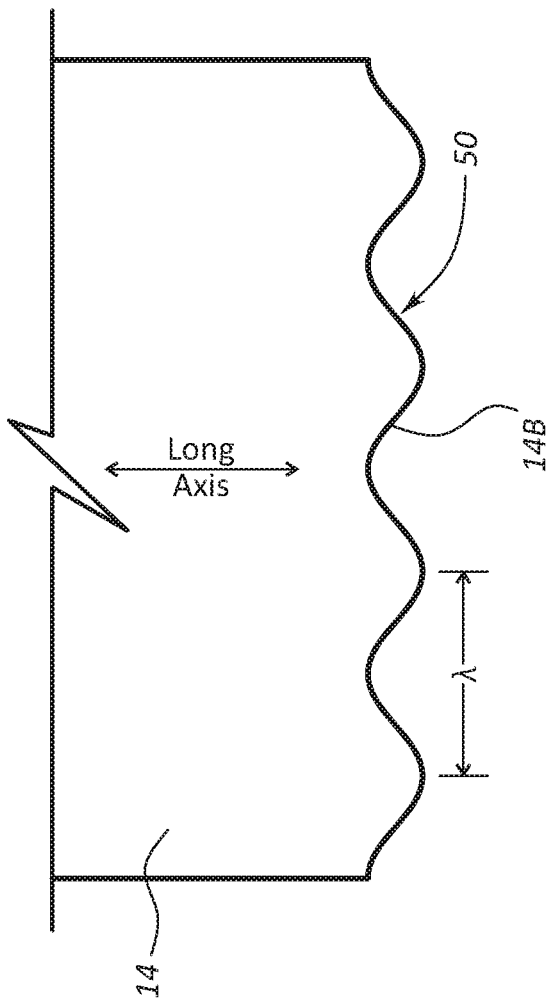
FIG. 6 is an unrolled view of an introducer sheath according to one embodiment.
Figure 7:
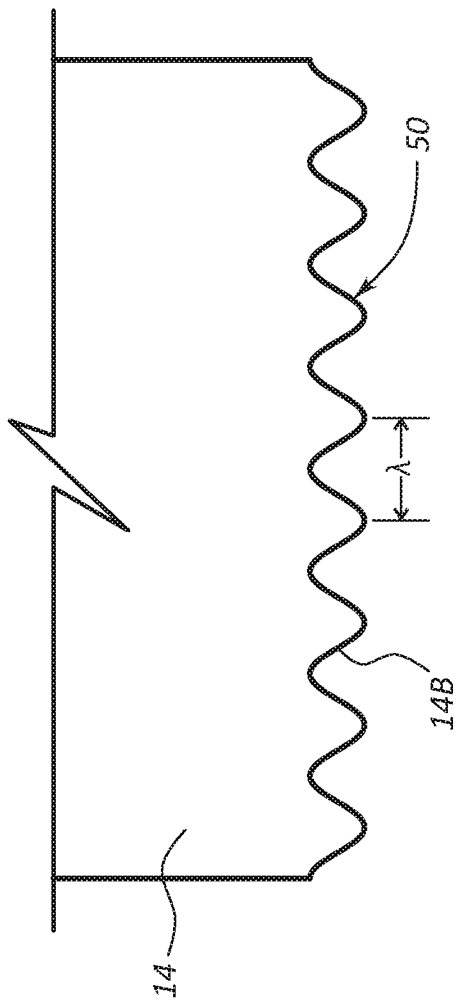
FIG. 7 is an unrolled view of an introducer sheath according to one embodiment.

FIG. 5 depicts the introducer 10 according to another embodiment, wherein the annular distal end 14B of the sheath tubular portion 14 defines a wavy, periodically repeating perimeter so as to define a plurality of periodic undulations 50. The undulations 50 are seen in clarity in FIG. 6, which depicts the tubular portion 14 of the sheath 12 unrolled and flattened. FIG. 6 shows that the undulations 50 are periodically sinusoidal in shape such that they repeat with a predetermined wavelength λ along the perimeter of the distal end 14B. For the embodiment shown in FIG. 6, for example, four undulations 50 are included on the perimeter of the distal end 14B. The number and size of the undulations 50 can vary, as seen by FIG. 7, where eight undulations are shown, the wavelength being half that shown in FIG. 6. It is appreciated that the size, number, amplitude, wavelength, shape, and other configuration of the undulations can vary from what is shown and described herein. In one embodiment, the number of undulations 50 is divisible by 360 so as to provide a whole, non-fractional number of complete undulations along the perimeter of the tubular portion distal end 14B. Also, though shown as integrally fitting the perimeter of the tubular portion distal end 14B, in another embodiment the undulations 50 can be defined such that at least one undulation is truncated along the perimeter. In other embodiments the undulations can depart from sinusoidal waves in shape. These and other variations of the undulations are contemplated.

With the distal end 14B of the tubular portion 14 of the sheath 12 configured as described above and joined with the dilator 24 as shown in FIG. 5, it is appreciated that the undulations 50 on the perimeter of the distal end 14B distribute the point of contact of the sheath tubular portion as it is inserted through the skin and into a vessel. Thus the insertion force is distributed as a function of longitudinal distance along the distal portion of the sheath tubular portion 14, which results in a smoother, less traumatic insertion as the introducer 10 passes through the skin and enters the vessel.

It is appreciated that the undulations 50 defined on the perimeter sheath tubular portion 14 as seen in FIGS. 5-7 can be manufactured by any suitable mode, including machining, molding, extrusion, cutting, casting, etc.

In one embodiment, it is appreciated that the introducer 10 can be configured so as to include both a cylindrical recess, similar to those shown in FIGS. 1A-3, and a wave-like sheath tubular portion distal end including undulations, similar to those shown in FIGS. 5-7. In this case, the distal end 40B of the cylindrical recess 40 would be configured to include a wave-like perimeter to correspond with the undulations 50 of the sheath tubular portion distal end 14B. In another embodiment, the distal end of the cylindrical recess includes no surface corresponding to the undulations, and only the distal end of the tubular portion includes the undulations. These and other variations are therefore contemplated.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An introducer, comprising:
  a sheath including a tubular portion defining a lumen, the tubular portion having an outer diameter from a proximal end to a distal end of the tubular portion;
  a dilator removably disposed in the lumen of the tubular portion of the sheath, the dilator including:
    a tapered distal tip; and
    an elongate body defining a cylindrical recess proximally extending from the tapered distal tip, the tubular portion of the sheath disposed in the cylindrical recess in an insertion configuration such that a gap is formed between the distal end of the tubular portion and a distal end of the cylindrical recess; and
  a filler material disposed in the gap to provide a transition between the sheath and the dilator.

2. The introducer as defined in claim 1, wherein the elongate body of the dilator defines a central guidewire channel, the cylindrical recess being coaxial to the central guidewire channel.

3. The introducer as defined in claim 1, wherein the distal end of the cylindrical recess is angled with respect to a line parallel to a longitudinal axis of the elongate body of the dilator.

4. The introducer as defined in claim 3, wherein the distal end of the tubular portion of the sheath defines an angle corresponding to the angled distal end of the cylindrical recess.

5. The introducer as defined in claim 1, wherein the filler material includes one of a gel, a resin, and an epoxy.

6. The introducer as defined in claim 1, wherein the filler material includes a dissolvable material.

7. The introducer as defined in claim 1, wherein the sheath includes PTFE and wherein the dilator includes HDPE, the sheath further including a hub that is configured to threadably engage a hub of the dilator.

8. The introducer as defined in claim 7, wherein the cylindrical recess extends proximally from the tapered distal tip of the dilator to the hub of the dilator.

9. The introducer as defined in claim 1, wherein the tapered distal tip has a maximum diameter less than the outer diameter of the tubular portion of the sheath i-s-when the tubular portion of the sheath is received within the cylindrical recess.

10. The introducer as defined in claim 1, wherein the tapered distal tip has a maximum diameter substantially equal to the outer diameter of the tubular portion of the sheath when the tubular portion of the sheath is received within the cylindrical recess.

11. The introducer as defined in claim 1, wherein the tapered distal tip has a maximum diameter greater than the outer diameter of the tubular portion of the sheath when the tubular portion of the sheath is received within the cylindrical recess.

12. An introducer, comprising:
  a sheath including a sheath hub and a tubular portion extending from the sheath hub, the tubular portion defining a lumen and having an outer diameter from a proximal end to a distal end of the tubular portion; and
  a dilator including:
    a dilator hub;
    a tapered distal tip having a maximum diameter greater than the outer diameter of the tubular portion of the sheath;
    an elongate body extending from the dilator hub and terminating at the tapered distal tip, the elongate body configured to be removably disposed in the lumen of the tubular portion of the sheath such that the tapered distal tip of the dilator distally extends past the distal end of the tubular portion of the sheath, the elongate body defining a cylindrical recess proximally extending from the tapered distal tip to the dilator hub, the cylindrical recess configured to receive the tubular portion of the sheath, wherein the tubular portion of the sheath is disposed in the cylindrical recess in an insertion configuration such that a gap is formed between the distal end of the tubular portion and a distal end of the cylindrical recess; and a filler material disposed in the gap to provide a transition between the sheath and the dilator.

13. The introducer as defined in claim 12, wherein the distal end of the tubular portion of the sheath is disposed proximate a distal end of the cylindrical recess, the distal end of the cylindrical recess defined adjacent the tapered distal tip of the dilator.

14. The introducer as defined in claim 13, wherein the distal end of the cylindrical recess is angled with respect to a line parallel to a longitudinal axis of the elongate body of the dilator.

15. The introducer as defined in claim 14, wherein the distal end of the tubular portion of the sheath defines an angle corresponding to the angled distal end of the cylindrical recess.

16. The introducer as defined in claim 14, wherein the angled distal end of the cylindrical recess comprises an acute angle.

17. The introducer as defined in claim 12, wherein the filler material is dissolvable.

\* \* \* \* \*